(12) United States Patent
Kubota et al.

(10) Patent No.: US 7,927,279 B2
(45) Date of Patent: Apr. 19, 2011

(54) ULTRASONOGRAPH, METHOD FOR DISPLAYING INFORMATION ON DISTORTION OF BIOLOGICAL TISSUE IN ULTRASONIC IMAGE

(75) Inventors: Jun Kubota, Chiba (JP); Hirotaka Baba, Chiba (JP)

(73) Assignee: Hitachi Medical Corporation, Tokyo (JP)

( * ) Notice: Subject to any disclaimer, the term of this patent is extended or adjusted under 35 U.S.C. 154(b) by 1309 days.

(21) Appl. No.: 10/516,598

(22) PCT Filed: Jun. 4, 2003

(86) PCT No.: PCT/JP03/07080
§ 371 (c)(1),
(2), (4) Date: Dec. 3, 2004

(87) PCT Pub. No.: WO2004/004574
PCT Pub. Date: Jan. 15, 2004

(65) Prior Publication Data
US 2005/0187470 A1   Aug. 25, 2005

(30) Foreign Application Priority Data

Jun. 4, 2002   (JP) ................................ 2002-162288

(51) Int. Cl.
A61B 8/00   (2006.01)
(52) U.S. Cl. ......... 600/443; 600/444; 600/445; 600/446
(58) Field of Classification Search .................. 600/443, 600/407, 437
See application file for complete search history.

(56) References Cited

U.S. PATENT DOCUMENTS 4,790,321 A   12/1988 Miwa et al.
5,143,070 A   9/1992 Ophir et al.
(Continued)

FOREIGN PATENT DOCUMENTS

CN   1207889 A   2/1999
(Continued)

OTHER PUBLICATIONS

L. Gao et. al., "Imaging of the Elastic Properties of Tissue—A Review", 1996, Ultrasound in Medicine and Biology, vol. 22, No. 8, pp. 959-977.*

(Continued)

*Primary Examiner* — Brian Casler
*Assistant Examiner* — Nasir Shahrestani
(74) *Attorney, Agent, or Firm* — Antonelli, Terry, Stout & Kraus, LLP.

(57) ABSTRACT

An ultrasonograph comprising a probe for measurement by bringing the probe into contact with a subject in a first state, first image creating means for creating a first image of the subject from the information sent from the probe, image display means for displaying the first image created by the first image creating means, means for setting at least one piece of reference information on the first image displayed by the image displaying means, second image creating means for creating a second image of the subject from the measurement information collected by bringing the probe into contact with the subject in a second state different from the first state, means for collecting information on the distortion of a desired region of interest in the second image on the basis of the variation, in the second image, of the reference information set on the first image by the setting means, and display control means for controlling the display of the distortion information collected by the distortion collecting means on the image display means.

17 Claims, 9 Drawing Sheets

U.S. PATENT DOCUMENTS

| | | | | |
|---|---|---|---|---|
| 5,265,612 | A | * | 11/1993 | Sarvazyan et al. ............ 600/471 |
| 5,524,636 | A | * | 6/1996 | Sarvazyan et al. ............ 600/587 |
| 5,606,971 | A | * | 3/1997 | Sarvazyan .................... 600/438 |
| 5,615,680 | A | | 4/1997 | Sano |
| 5,678,565 | A | * | 10/1997 | Sarvazyan .................... 600/587 |
| 5,895,358 | A | | 4/1999 | Becker et al. |
| 6,099,471 | A | * | 8/2000 | Torp et al. .................... 600/438 |
| 6,494,840 | B1 | * | 12/2002 | Mak et al. .................... 600/446 |
| 7,050,610 | B2 | * | 5/2006 | Chen et al. ................... 382/128 |

FOREIGN PATENT DOCUMENTS

| | | | |
|---|---|---|---|
| JP | 03-194947 | A | 8/1991 |
| JP | 05-317313 | | 12/1993 |
| JP | 2000-060857 | A | 2/2000 |
| JP | 2000060857 | * | 2/2000 |
| JP | 2000-229081 | A | 8/2000 |
| WO | WO 91/07657 | | 5/1991 |

OTHER PUBLICATIONS

Y. Yamashita et al, "Ultrasonic Imaging of Elasticity of Soft Tissue Based on Measurement of Internal Displacement and Strain," 1995 IEEE Ultrasonics Symposium, pp. 1207-1211.*

M. O'Donnell et al, "Internal Displacement and Strain Imaging Using Ultrasonic Speckle Tracking," May, 1994, IEEE Transactions on Ultrasonics, Ferroelectrics, and Frequency Control, vol. 41, No. 3, May, 1994.*

J. Ophir et al, "Elastographic Imaging," 2000, Ultrasound in Medicine and Biology, vol. 26, Supplement 1, pp. S23-S29.*

Y. Yamashita et al, 1994 IEEE Ultrasonics Symposium, pp. 1449-1453.*

Japanese Office Action dated Sep. 19, 2008, issued in corresponding Japanese Patent Application No. 2002-162288.

T. Shiina EISUM8, E. Ueno Jsum, M. Ito and T. Mochzuki, Development of 3-D Ultrasonic Tissue Elasticity CT, Univ. of Tsukuba, Tokyo J Med Ultrasonics, vol. 28, No. 3 (2001).

* cited by examiner

Image data point P(x,y) within circle whose radius is r, after filtering

Point concerned O(x,y)

Distribution of powers subjected to cross-correlation

ULTRASONOGRAPH, METHOD FOR DISPLAYING INFORMATION ON DISTORTION OF BIOLOGICAL TISSUE IN ULTRASONIC IMAGE

TECHNICAL FIELD

The present invention relates to a diagnostic ultrasound system which time-sequentially obtains ultrasonic images (ultrasonic cross-section images) while varying of pressure applied to a biological body (subject) using a probe, and which diagnoses hardness or softness of a biological tissue by utilizing a difference between ultrasonic images.

BACKGROUND ART

In conventional diagnostic ultrasound systems, as described in Japanese Patent No. 3194947 and U.S. Pat. No. 5,143,070, when an examining physician such as a paramedic applies extraneous force to a body surface of a region-of-interest in a subject using a probe, a difference between ultrasonic cross-section images of different frames is produced in order to measure a displacement caused by applying the extraneous force. The conventional arts make it possible to diagnosis hardness or softness of each biological tissue in the region-of-interest.

However, the above patent documents merely describe displaying a contour image of distortion and Young's modulus values. The conventional diagnostic ultrasound systems cannot cope with the need for time-sequentially acquiring ultrasonic images while varying the pressure applied to a body surface by giving force to a probe, and producing a difference between ultrasonic images so as to visualize the hardness or softness of a biological tissue.

DISCLOSURE OF INVENTION

The foregoing drawback is overcome by a diagnostic ultrasound system including: a probe for ultrasonic measurement by bringing said probe into contact with a subject in a first state; a first image production means for producing a first image of the subject according to information received from the probe; an image display means for displaying the first image produced by the first image production means; a means for setting at least one piece of reference information on the first image displayed by the image display means; a second image production means for producing a second image of the subject according to information measured by bringing the probe into contact with the subject in a second state different from the first state; a variation operation means for calculating a change of the reference information, which is set on the first image by the setting means, into a counterpart visualized in the second image; a distortion operation means for calculating distortion information on a desired region-of-interest delineated in the second image according to the change calculated by the variation operation means; and a display control means for controlling the display of distortion information, which is calculated by the distortion operation means, on the image display means.

Moreover, aside from the foregoing hardware configuration, a computer system included in the diagnostic ultrasound system or a general-purpose computer may implement a method of displaying distortion information on a biological tissue observed in an ultrasonic image; the method including a step for time-sequentially storing displacements of a biological tissue in a memory means, a step for time-sequentially reading the displacements from the memory, a step for displaying distortion information on a biological tissue that the relative displacements can be relatively observed.

BEST MODE FOR CARRYING OUT THE INVENTION

Referring to the appended drawings, an embodiment of the present invention will be described below.

Figure 1:
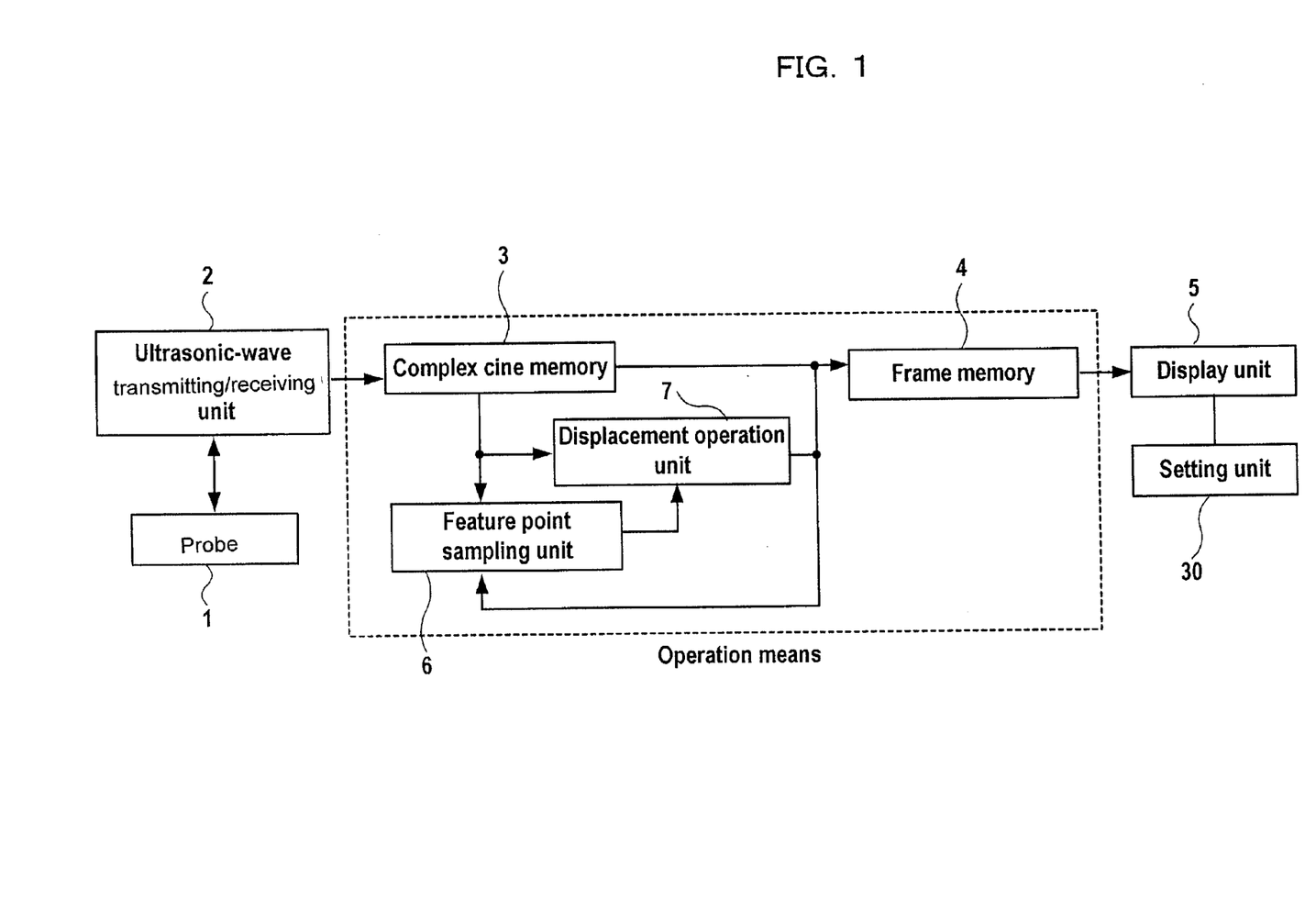
FIG. 1 shows a schematic block diagram for explaining a diagnostic ultrasound system in accordance with an embodiment of the present invention.

FIG. 1 shows a schematic block diagram for explaining a diagnostic ultrasound system in accordance with an embodiment of the present invention.

The diagnostic ultrasound system in accordance with the embodiment includes: a probe (ultrasonic probe) 1; an ultrasonic-wave transmitting/receiving unit 2 electrically connected to the probe 1; a complex cine memory 3 electrically connected to the ultrasonic-wave transmitting/receiving unit 2; a frame memory 4 electrically connected to the complex cine memory 3; a display unit 5 electrically connected to the frame memory 4; a feature point (reference information) sampling unit 6 electrically connected to each of the complex cine memory 3 and frame memory 4; a displacement operation unit 7 electrically connected to each of the complex cine memory 3, frame memory 4, and feature point sampling unit 6, and a setting unit 30 electrically connected to the display unit 5.

An operation means has the capabilities of the complex cine memory 3, frame memory 4, feature point sampling unit 6, and displacement operation unit 7.

The probe 1 is a known probe which transmits or receives ultrasonic waves to or from a subject so that mechanically or electronically beam scan is carried out. The probe 1 includes one or more transducers (transducer elements) which serve as a source of ultrasonic waves and receive echoes reflected from a subject in a biological body.

The ultrasonic-wave transmitting/receiving unit 2 drives the probe 1 for generation of ultrasonic waves, and handles electric signals (echo signals) outputted from the transducer elements according to reflected echoes. The ultrasonic-wave transmitting/receiving unit 2 includes a known transmission pulser and transmission delay circuit for producing an ultrasonic beam to be transmitted from the probe 1 to a subject, a reception amplifier which amplifies echo signals received by the each transducers arrayed in the probe 1, and a phasing/adding circuit which arranges and adds the phase of the amplified input reflective echo signal.

In the complex cine memory 3, echo signals which are phased by the ultrasonic-wave transmitting/receiving unit 2 are time-sequentially stored as pieces of frame information representing a plurality of frames in the form of complex numbers or absolute values and phase angles.

The frame memory 4 produces image data by storing the 5 frame information received from the complex cine memory 3 every scanning line according to ultrasonic beam. The frame memory 4 includes an affine transformation circuit which transforms scanning lines according to ultrasonic beam into scanning lines on a TV monitor, an image data memory, and an overlay circuit which displays color information, character string information, and graphic information on the display unit 5 while superposing them on one another.

The display unit 5 displays an image according to a signal outputted from the frame memory 4. The display unit 5 has, for example, a TV monitor which receives a television signal representing a B-mode image (cross-section image) and on which the cross-section image is displayed.

Figure 11A:
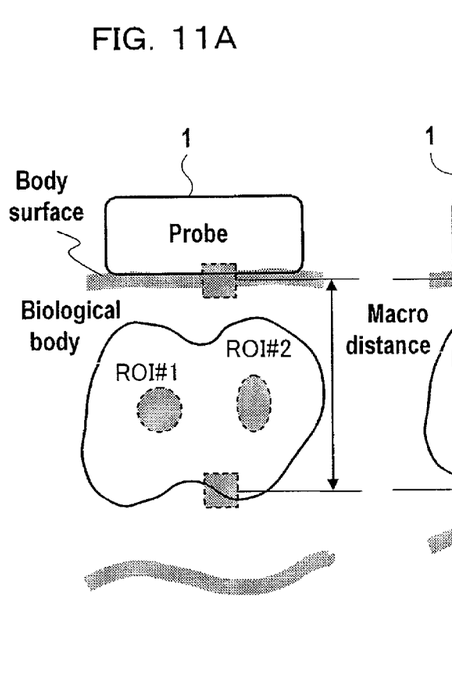
FIG. 11 shows positional relationships between a region-of-interest in a subject and a probe attained before and after a pressure load is applied according to the embodiment.

The feature point sampling unit 6 extracts a feature point which copes with time-sequential data (time-series cross-section image) stored in the complex cine memory 3 and a pre-displacement (initial) cross-section image produced by the displacement operation unit and stored in a memory. Herein, the pre-displacement image is, as shown in FIG. 11A, an image based on echo signals acquired when the distance of a feature point or a region-of-interest, which is located at the deepest position relative to the vicinity of the probe, from the vicinity of the probe (macro distance) is the largest. As shown in FIG. 11A, before the probe 1 is pressed against a subject, a biological tissue and a plurality of local region-of-interest (ROI#1 and ROI#2) do not change.

Figure 11B:
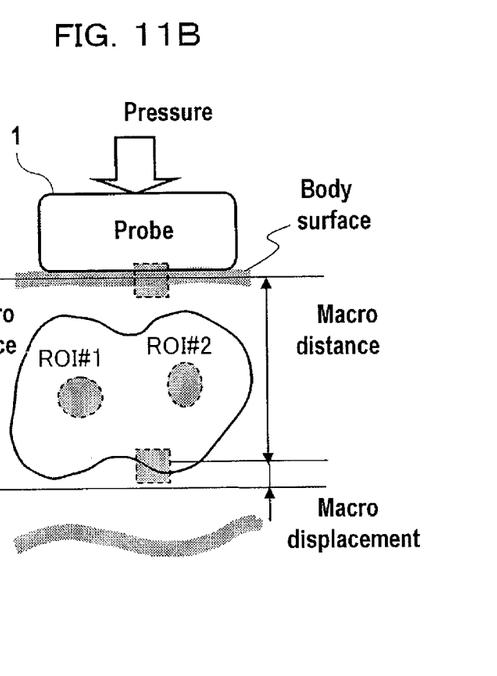
Figure 12A:
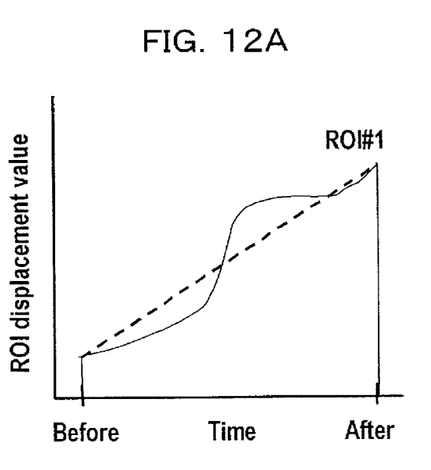
FIG. 12 shows graphs concerned in the relationships of image display parameters to time.
Figure 12B:
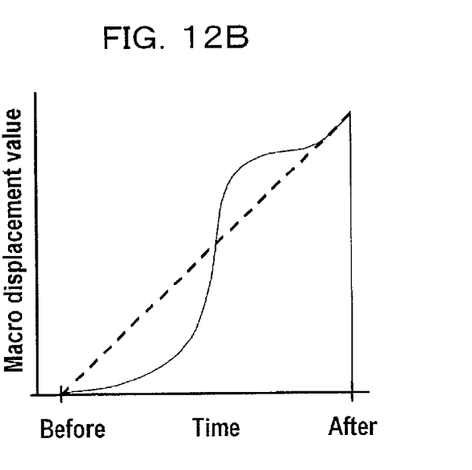

Meanwhile, as shown in FIG. 11B, a post-displacement image based on echo signals is acquired when the macro distance of the region-of-interests which is located at the deepest position, from the probe is the smallest. As shown in FIG. 11B, after the probe 1 is pressed against a subject, the biological tissue and the a plurality of local region-of-interest (ROI#1 and ROI#2) in the biological tissue are, compared with those shown in FIG. 11A, deformed as if to contract. The deformation is attributable to a micro displacement made by a region-of-interest and a macro displacement made by an entire biological body. The micro displacement and macro displacement have a difference indicated in FIG. 12. FIG. 12A shows the micro displacements made by a region-of-interest with the passage of time before and after pressure is applied to the body surface. FIG. 12B shows the macro displacements made by the biological body with the passage of time before and after pressure is applied to the body surface. In other words, the macro displacement and micro displacement show inherent time-series changes before and after pressure is applied. The feature point sampling unit 6 will be detailed later.

The displacement operation unit 7 compares the feature point and counterpart, which are extracted by the feature point sampling unit 6 before and after deformation, with each other, and calculates a variation of deformation made by a region-of-interest located at the feature point on the basis of the result of the comparison. The displacement operation unit 7 is designed to act according to whether a feature point and its counterpart are detected by the feature point sampling unit 6. The displacement operation unit 7 includes: a means for deforming information stored in the complex cine memory so that the feature point and counterpart will be agreed with each other; a means for sequentially preserving a variation of movement derived from deformation (a variation of deformation) as a value of a displacement made by the region-of-interest; and a means for sequentially comparing the preserved displacement values with one another so as to calculate maximum and minimum displacement values indicating displacements made by the region-of-interest. Moreover, since only the maximum and minimum displacement values indicating displacements made by the region-of-interest are calculated, an intermediate value of all displacement values indicating displacements made by the region-of-interest or a displacement width by which the region-of-interest is displaced in total may be calculated. The displacement operation unit 7 will be detailed later.

The setting unit 30 is used to set arbitrary position in a cross-section image of a subject displayed on the display unit 5 as the position of a region-of-interest. The setting unit 30 is also used to define various settings of the diagnostic ultrasound system for production of images.

When the feature point and counterpart detected by the feature point sampling unit 6 are represented by mutually different coordinates, that is, the coordinates (positions) representing the feature point and counterpart are different from each other, the displacement operation unit 7 included in the present embodiment acts as described below. First, information read from the complex cine memory 3 is deformed so that the feature point and counterpart will agree with each other. The deformed information and the information that is not deformed are compared with each other in order to calculate a variation of deformation as a displacement value. Furthermore, maximum and minimum displacement values are preserved. An image in which the feature point is seen to have been displaced to a variation indicated with the minimum displacement value is preserved as an initial image, and an image in which the feature point is seen to have been displaced to a variation indicated with the maximum displacement value is preserved as a final image produced after displacement. On the other hand, if the coordinates (positions) of the feature point and counterpart had no difference, or if the counterpart of the feature point were not found, the displacement operation unit 7 would continue to preserve an initial image and a final image that are stored immediately previously.

A block may be interposed between the feature point sampling unit 6 and the displacement operation unit 7: the block for verifying whether the counterpart of a feature point is found or whether the feature point has moved. Nevertheless, the same advantage as the foregoing one can be provided by the displacement operation unit 7.

Next, referring back to FIG. 1, a description will be made of acquisition of images showing different distortions, which are derived from application of pressure to a subject, using the diagnostic ultrasound system in accordance with the present invention.

According to the present embodiment, the probe 1 is used to apply pressure during transmission or reception of ultrasonic waves in order to produce images. Echo signals which are signals corresponding to echoes received by the transducers are sequentially transferred to the ultrasonic-wave transmitting/receiving unit 2. After the echo signals are phased and added up, a resultant signal is transmitted to the complex cine memory 3. In the complex cine memory 3, a plurality of frames, that is, a plurality of cross-section images is time-sequentially stored together with their phase information. The stored cross-section images are sequentially outputted to each of the frame memory 4, feature point sampling unit 6, and displacement operation unit 7.

The feature point sampling unit 6 compares an image read from the complex cine memory 3 with a pre-displacement image received from the displacement operation unit 7, and extracts a feature point and its counterpart. The coordinates of the feature point and counterpart extracted by the feature point sampling unit 6 are outputted to the displacement operation unit 7. The image read from the complex cine memory 3 is deformed so that the feature point and counterpart will be agreed with each other. The image that has been deformed and the image that is not deformed are compared with each other in order to calculate a variation of deformation. The variation of deformation is regarded as a displacement value. The displacement value is compared with the maximum and minimum displacement values which are stored. Only when the displacement value exceeds the maximum value or is smaller than the minimum value, the maximum or minimum value is updated to the newly calculated displacement value. At this time, if the updated displacement value were the minimum displacement value, the previous initial image would be updated to the image in which the feature point is seen to have been displaced to a variation indicated with the minimum displacement value. On the other hand, when the updated displacement value were the maximum displacement value, the previous post-displacement final image would be updated to the image in which the feature point is seen to have been displaced to a variation indicated with the maximum displacement value. The maximum and minimum displacement values are transmitted as the maximum and minimum displacement values indicating the variations of displacements made by a region-of-interest to the frame memory 4. The initial image is transmitted as an image, in which the region-of-interest is seen to have been displaced by a variation indicated with the minimum displacement value, to the frame memory 4. Moreover, the post-displacement final image is transmitted as an image, in which the region-of-interest is seen to have been displaced by a variation indicated with the maximum displacement value, to the frame memory 4. Consequently, an image for displaying is constructed according to a cross-section image which is transmitted from both of the complex cine memory 3 and measured in real time, and a distortion image produced based on the maximum and minimum displacement values transmitted from the displacement operation unit 7 and the initial image and post-displacement final image. The image which is constructed for displaying is then displayed on the display area of the display unit 5.

For example, a difference image is produced based on the post-displacement final image and initial image according to a known technique. The difference image is displayed as the distortion image together with a cross-section image, which is measured in real time, on the display unit 5.

Figure 13:
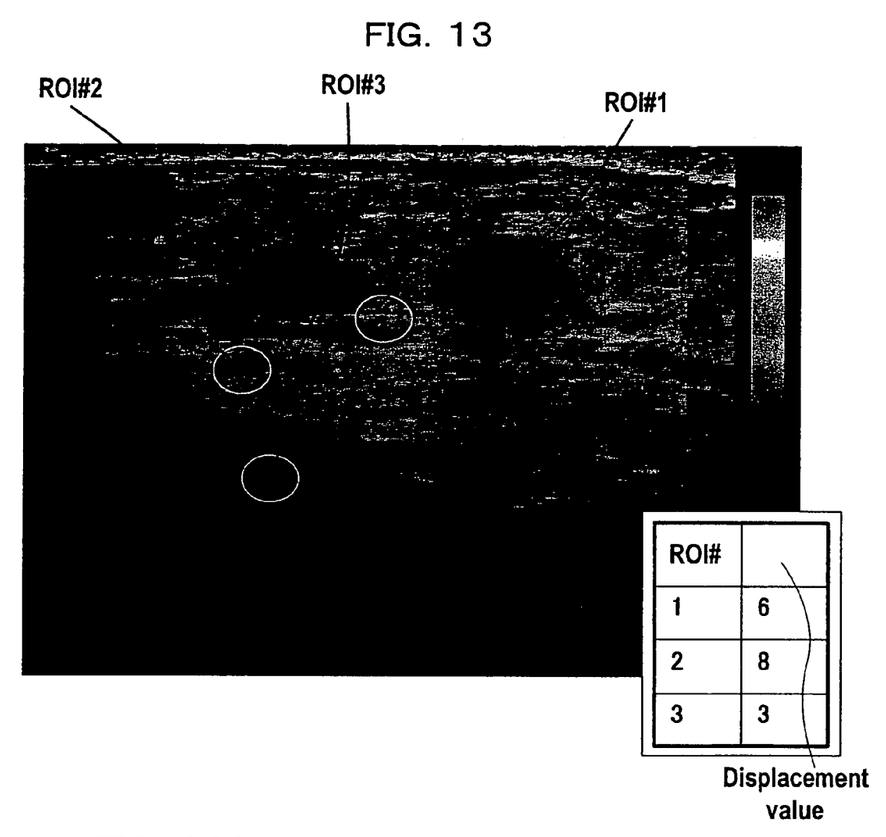
FIG. 13 shows an example of the display on a display device.

The distortion image is, as shown in FIG. 13, displayed in gray-scale in colors while superposed on a cross-section image. A plurality of region-of-interest ROI#1, ROI#2, ROI#3 is delineated as desired region-of-interest by use of the setting unit 30. Namely, the displacement values indicating the variations of displacements made by the designated regions of interest ROI#1, ROI#2, and ROI#3 are displayed as shown in the right lower part of the drawing. Data representing a distortion image (a difference between cross-section images) are produced through arithmetic operations so as to display the numerical values. For example, a known character string generator converts the image data into characters, and the characters are displayed in the cells in a table allocated to ROI#1, ROI#2, and ROI#3. Because the cross-section image and distortion image are measured in real time, an instantaneous value that updates in real time is displayed. Instantaneous values may be sequentially stored in a memory in order to calculate statistics including a cumulative value and an average, and the statistics may be displayed. The statistics including the cumulative value, average, variance, and standard deviation may be calculated according to a known statistical data calculating method. Moreover, the number of statistics displayed may not be one, but a plurality of statistics, for example, the instantaneous value and average may be displayed in combination. Moreover, a macro displacement that is a displacement made by a biological body may also be displayed.

Figure 14A:
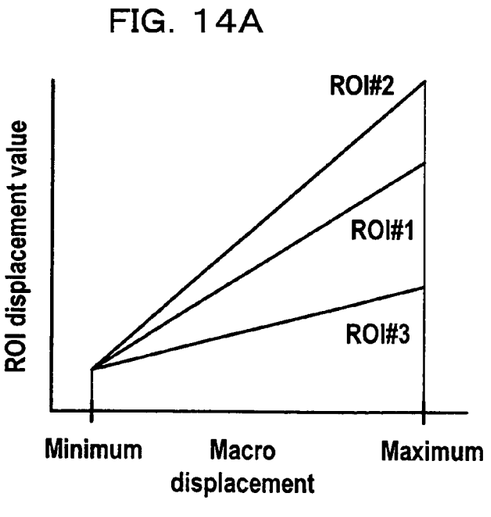
FIG. 14 shows another example of the display on the display device different from that shown in FIG. 13.
Figure 14B:
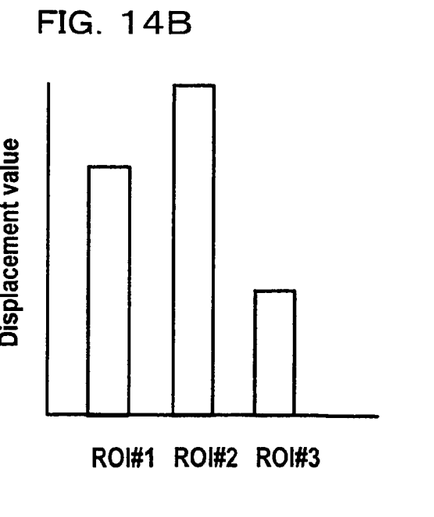

Moreover, instead of the numerical values shown in FIG. 13, or in combination with them, a graph shown in FIG. 14 may be displayed. For display of the graph, data representing a distortion image (a difference between cross-section image data items) is calculated through arithmetic operations, and a known graph generator converts the calculated data into a graph that can be displayed in a desired display area on the display unit. The graph produced is then displayed. FIG. 14A shows the relationship of displacements based on region-of-interest to the macro displacement based on a biological body. The graph makes it possible to verify at sight which of the region-of-interest exhibit local hardness. For example, in this example, because the displacement based on the region-of-interest ROI#3 is small, it means that a part of the region-of-interest ROI#3 is hard and suspected of being a malignant tumor. Consequently, the graph can provide a doctor with diagnostic information signifying that close examination is needed. Moreover, as shown in FIG. 14B, a bar graph permitting comparison of displacements made by regions of interest may be adopted. Even the bar graph can provide a doctor with diagnostic information similar to the one shown in FIG. 14A. Incidentally, aside from the bar graph, any of various graphs including a line graph, a solid bar graph, and a solid line graph, and a circular graph may be adopted.

Various display forms are conceivable. Namely, region-of-interest may be displayed in different manners, that is, in different colors or shapes. A locus of points indicating the position of an image attained before application of pressure and the positions of the image displaced after application of pressure may be displayed. The images produced before and after application of pressure may be displayed in different colors. One of the images produced before and after application of pressure may be displayed with a solid line and the other may be displayed with a dashed line. The images produced before and after application of pressure may be displayed while being superposed on each other. The images produced before and after application of pressure may be displayed side by side. Any of the display forms may be adopted independently or in combination.

Thus, a portion of an image showing different hardness can be displayed while being clearly distinguished from the other portion. Moreover, a distortion image can be produced without the necessity of a special stress application device. Accordingly, the maximum and minimum displacement values and the distortion image may be displayed together with a cross-section image sent from the complex cine memory 3, that is, a real-time cross-section image. Alternatively, the maximum and minimum displacement values and the distortion image may be displayed after acquisition of cross-section images is completed or responsively to handling of the setting unit 30.

As mentioned above, in the diagnostic ultrasound system of the present embodiment, the probe 1 is used to directly give a pressure to a region-of-interest. The displacement operation unit 7 uses cross-section images, which are sequentially measured, to calculate the maximum and minimum displacement values, which indicate maximum and minimum displacements made by a region-of-interest, in real time. Any special application device is unnecessary, and the time required for application of pressure is saved. Consequently, the time required for diagnosis is shortened. Eventually, a load incurred by an examining physician or a subject can be minimized.

Moreover, because an examining physician need not make a subjective judgment, objective ultrasonic examination can be achieved. Consequently, the examination time will be shortened.

Figure 2:
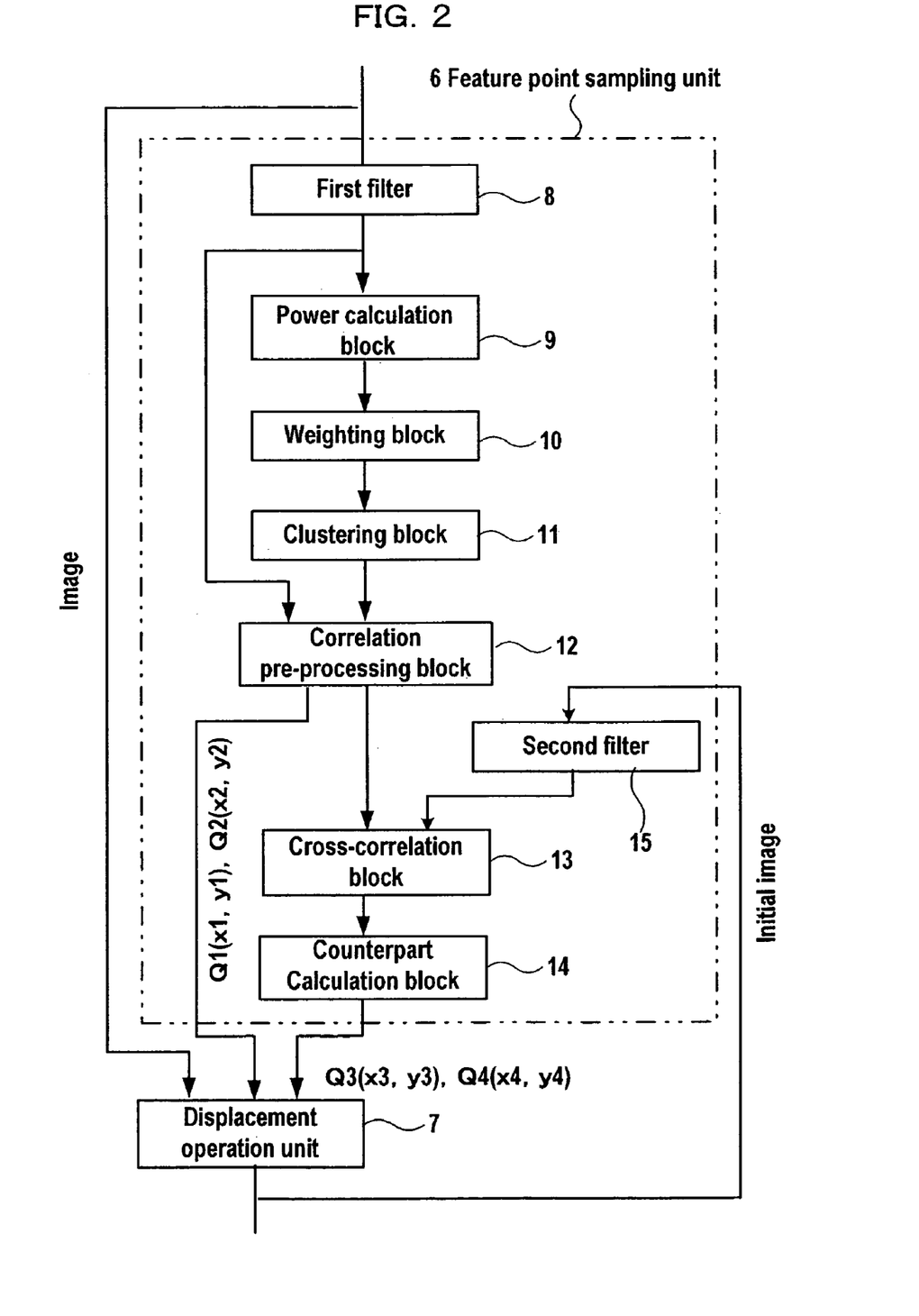
FIG. 2 shows a schematic block diagram for explaining a feature point sampling unit included in the embodiment.

FIG. 2 is an explanatory diagram schematically showing the configuration of the feature point sampling unit included in the present embodiment. As apparent from FIG. 2, the feature point sampling unit 6 included in the present embodiment comprises: a first filter 8; a power calculation block 9 electrically connected to the first filter 8; a weighting block 10 electrically connected to the power calculation block 9; a clustering block 11 electrically connected to the weighting block 10; a correlation pre-processing block 12 electrically connected to each of the first filter 8 and clustering block 11A cross-correlation block 13 electrically connected to each of the correlation pre-processing block 12 and a second filter 15; a counterpart calculation block 14 electrically connected to the cross-correlation block 13; and the second filter 15 electrically connected to the displacement operation unit 7.

Figure 9:
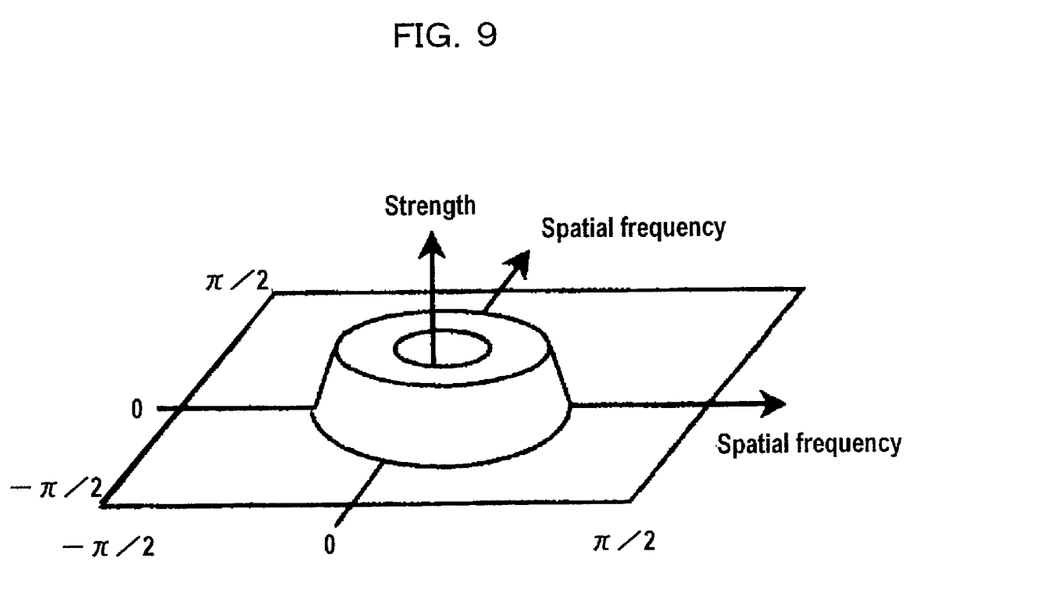
FIG. 9 shows a schematic drawing for explaining an action of a first filter included in the embodiment.
Figure 10:
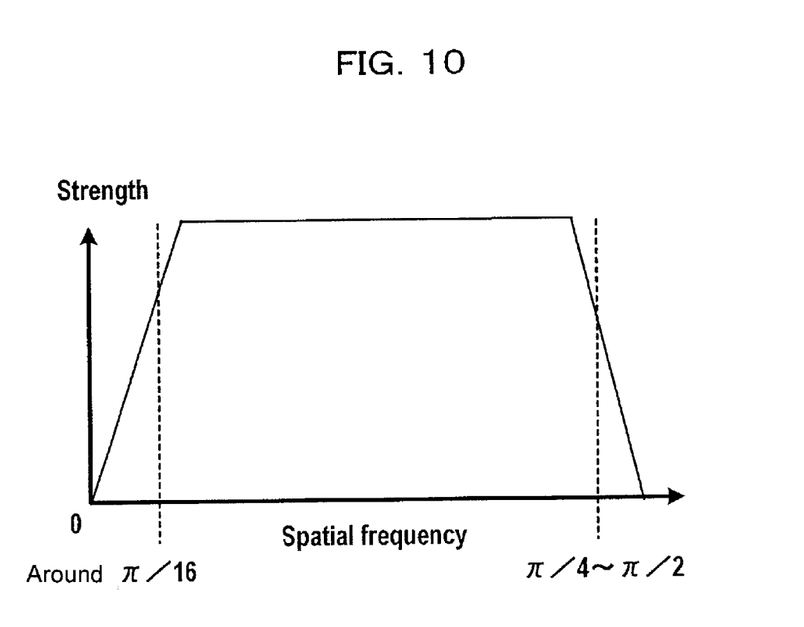
FIG. 10 shows a schematic drawing for explaining an action of the first filter included in the embodiment.

Referring to FIG. 2, the first filter 8 is a known filter that selectively passes image data which represents certain spatial frequencies and which is read from the complex cine memory 3. According to the present embodiment, the first filter 8 offers, as shown in FIG. 9, a passband in the form of a concentric circle with a spatial frequency of 0 as a center point. FIG. 10 is an explanatory diagram concerning the passband shown in FIG. 9. As apparent from FIG. 10, the first filter 8 included in the present embodiment is a bandpass filter that has a lower-limit cutoff frequency set to about $\pi/16$ and has an upper-limit cutoff frequency set to a range from about $\pi/4$ to $\pi/2$.

Figure 3:
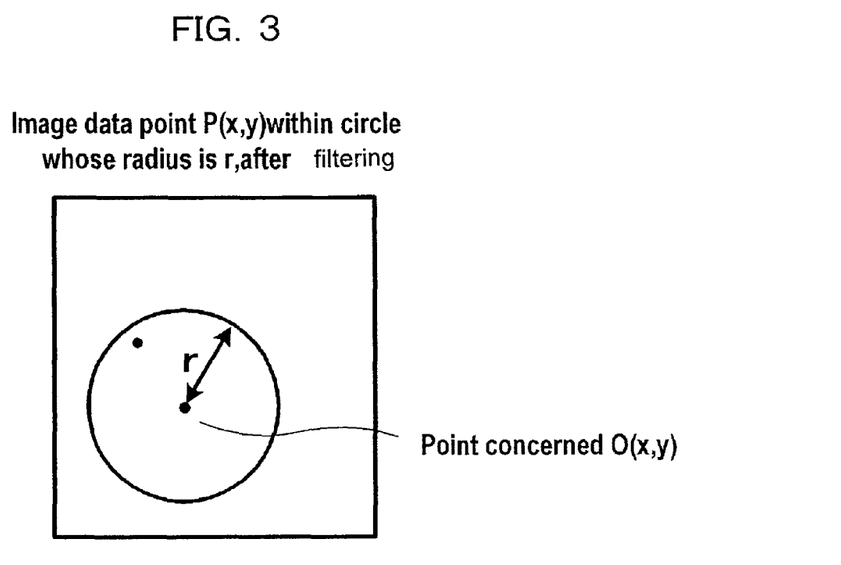
FIG. 3 shows a schematic drawing for explaining an image after filtered filtering according to the embodiment.

The power calculation block 9 is a means for calculating the powers of image data sent from the first filter 8. As shown in FIG. 3, the sum of the squares of data items at all points P(x, y) within a circle having a radius r with a point concerned O(x, y) as a center thereof is calculated as the power of data at the point O. The power calculation unit 9 performs this calculation on every point (x, y).

Figure 4:
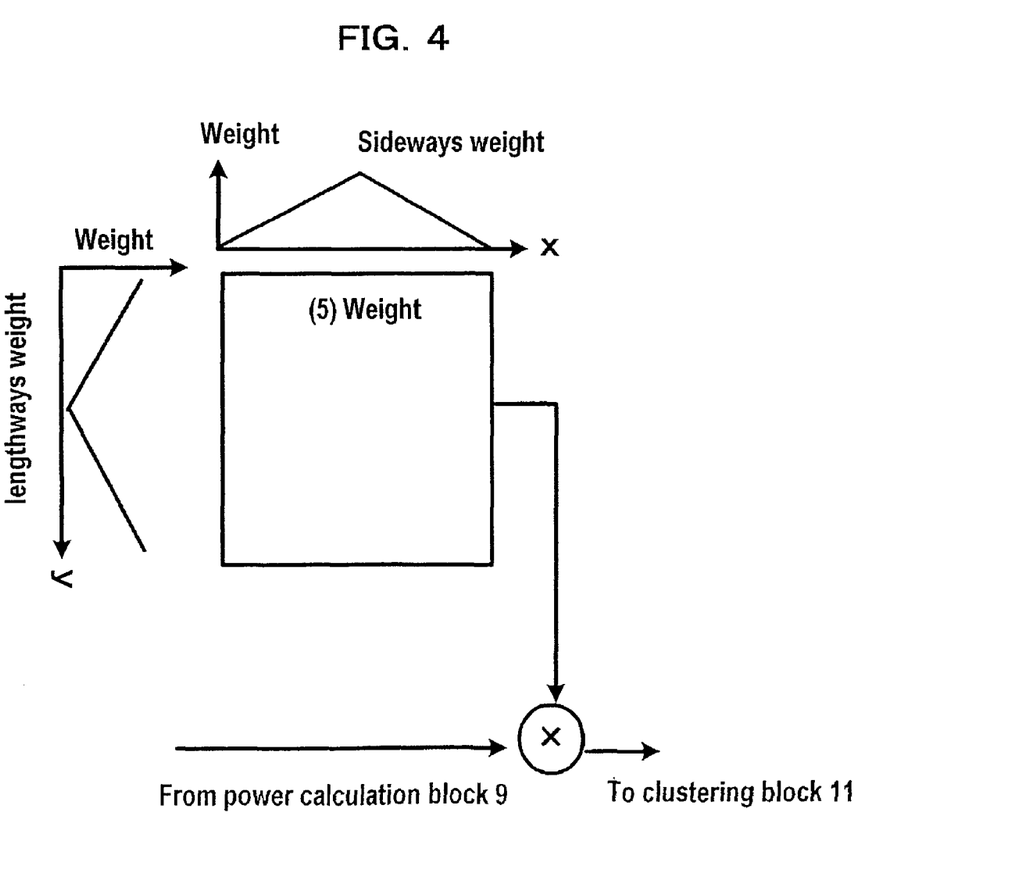
FIG. 4 shows a schematic diagram for explaining a weighting unit included in the embodiment.

The weighting block 10 is an operation means for applying a predetermined weight to the distribution of powers calculated by the power calculation block 9. The weight to be applied is, for example, as shown in FIG. 4, increased toward to a sideways center, and is decreased toward a lengthways center.

Figure 5:
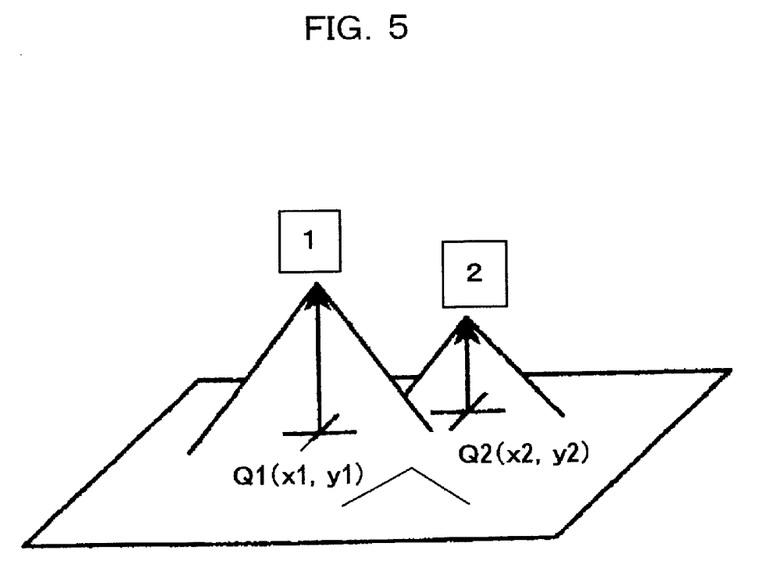
FIG. 5 shows a schematic drawing for explaining an action of a clustering unit included in the embodiment.

The clustering block 11 is a means for detecting two peak points in the distribution of powers sent from the weighting block 10, and retrieving values associated with the peak points. For example, as shown in FIG. 5, the coordinates (x1, y1) of the largest peak point and the associated value Q1 are retrieved as the first data, and the coordinates (x2, y2) of the second largest peak point and the associated value Q2 are retrieved as the second data. A known propagation deletion method or the like may be adopted as a method of separating or identifying a peak point from a two-dimensional distribution having a plurality of peak points.

Figure 6:
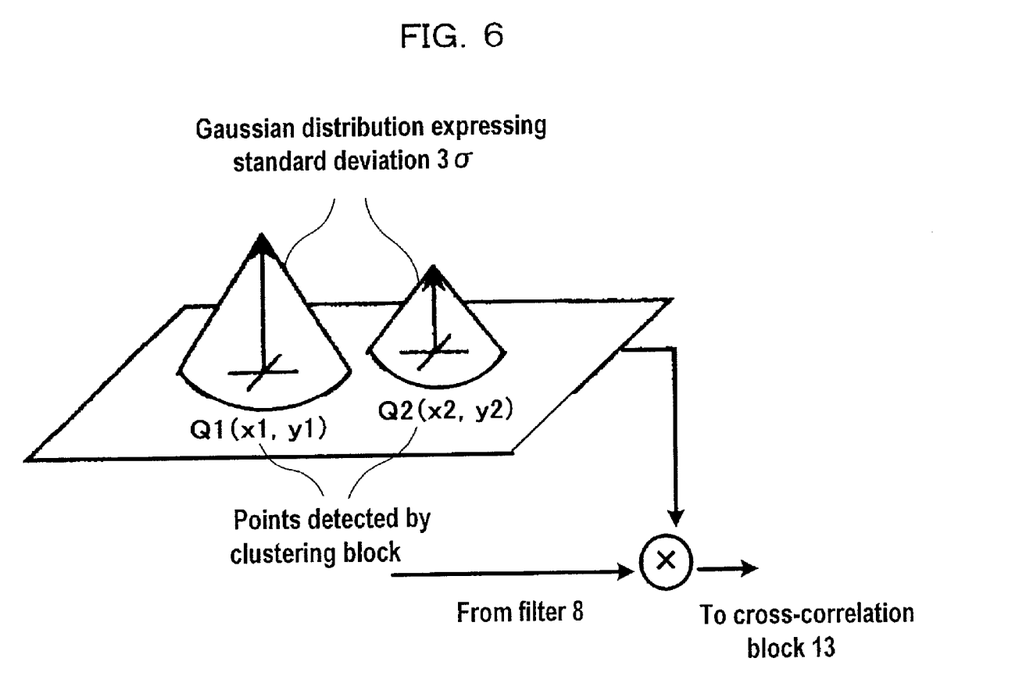
FIG. 6 shows a schematic drawing for explaining an action of correlation pre-processing unit included in the embodiment.

The correlation pre-processing block 12 is a means for fitting a predetermined weighting function to the coordinates of the two peak points and the associated values that are detected by the clustering block 11. For example, when a Gauss' curve expressing a Gaussian distribution is adopted as the graph of the weighting function, the weighting function is applied so that a Gaussian distribution expressing a standard deviation of $3\sigma$ will be produced to have each of the two peak points Q1(x1, y1) and Q2(x2, y2), which are associated with the values Q1 and Q2, as a center thereof. However, the weighting function is not limited to the Gauss' curve expressing the Gaussian distribution. Alternatively, the Hamming window function, Hanning window function, or Blackman-Harris window function will do.

The cross-correlation block 13 is a known means for calculating correlations between the distribution of weights sent from the correlation pre-processing block 12 and image data sent from the second filter 15.

Figure 7:
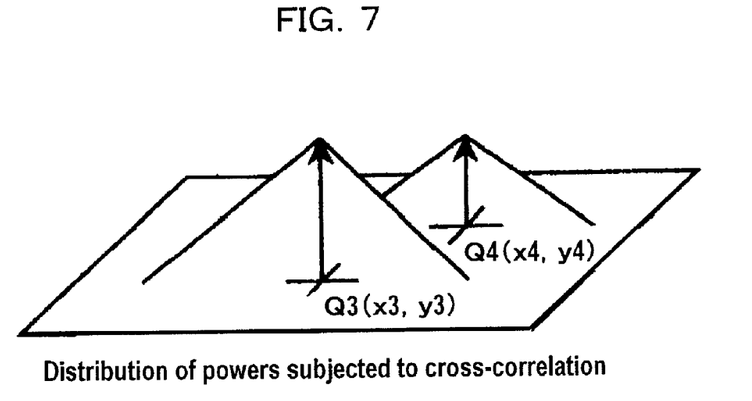
FIG. 7 shows a schematic drawing for explaining an action of a counterpart calculation block included in the embodiment.

The counterpart calculation block 14 searches a distribution of correlations received from the cross-correlation block 13 for two peak points and their associated values. The counterpart calculation block 14 performs arithmetic operations similar to those performed by the clustering block 11. As a result of the arithmetic operations performed by the counterpart calculation block 14 included in the present embodiment, for example, as shown in FIG. 7, the coordinates (x3, y3) and (x4, y4) representing the two peak points and the values Q3 and Q4 associated therewith are determined.

The second filter 15 is a means for selectively passing joint image data that represents certain spatial frequencies and is sent from the displacement operation unit 7. The second filter 15 performs processing similar to the one performed by the first filter 8.

Next, actions to be performed by the feature point sampling unit 6 included in the present embodiment will be described in conjunction with FIG. 2.

The first filter 8 selectively passes image data that is carried by a signal sent from the complex cine memory 3 and that represents certain spatial frequencies. Specifically, image data representing spatial frequencies ranging from $\pi/16$ to a range from $\pi/4$ to $\pi/2$ is sampled and transmitted to the power calculation block 9. The power calculation block 9 handles the received image data so as to calculate the sum of the squares of data items at all points P(x, y) within a circle having a radius r with respect to each of points concerned O(x, y). The calculated sums are transmitted as the powers of the data at all the points concerned O to the weighting block 10. The weighting unit 10 serves as an operation means for applying a predetermined weight to data representing the powers. At this time, the weight to be applied will be increased toward the sideways center of the data, and decreased toward the lengthways center of the data. The resultant data are transmitted to the clustering unit 11. The data received by the clustering unit 11 are subjected to, for example, known propagation deletion so that the coordinates of the two peak points and the associated values thereof will be detected. The detected coordinates and values are transmitted to the correlation pre-processing unit 12.

The correlation pre-processing unit 12 also receives an output of the first filter 8. The coordinates of the two peak points and the associated values thereof which are detected by the clustering block 11 are weighted according to the predetermined weighting function. The resultant data is transmitted to the cross-correlation block 13. The cross-correlation block 12 calculates correlations (or a distribution of correlation values) of the received data with image data sent from the second filter, and transmits the distribution of correlations to the counterpart detection block 14. The counterpart detection block 14 having received the distribution of correlations performs arithmetic operations similar to those performed by the clustering block 11 so as to detect the coordinates of two peak points and the associated values thereof. Consequently, the coordinates (x3, y3) and (x4, y4) of the two peak points and the values Q3 and Q4 thereof are transmitted to the displacement operation unit 7.

Figure 8:
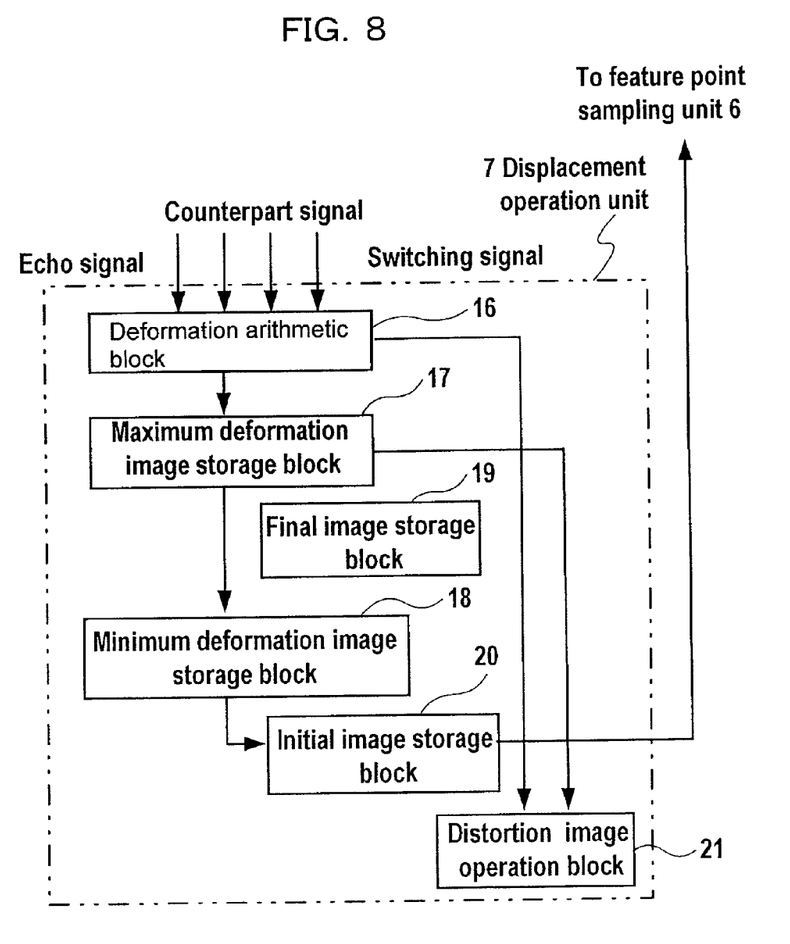
FIG. 8 shows a schematic block diagram for explaining a displacement operation unit included in the embodiment.

FIG. 8 is an explanatory diagram schematically showing the configuration of the displacement operation unit included in the present embodiment.

As apparent from FIG. 8, the displacement operation unit 7 included in the present embodiment comprises a deformation arithmetic block 16, a maximum deformation image storage block 17, a minimum deformation image storage block 18, a final image storage block 19, an initial image storage block 20, and a distortion image operation block 21.

Referring to FIG. 8, the deformation arithmetic block 16 is a means for calculating as data signals distance between a feature point and a counterpart which are associated with each other by the counterpart calculation block 14 and a direction of movement made by the feature point.

The maximum deformation image storage block 17 is a means for identifying and storing beam data signals of an image in which the feature points is seen to have deformed to the greatest extent.

The minimum deformation image storage block 18 is a means for identifying and storing beam data signals of an image in which a distance between feature points including codes is smallest.

The final image storage block 19 is a means for storing an image in which a change of the feature points is greatest. The stored image is transmitted to the distortion image operation block 21.

The initial image storage block 20 is a means in which an initial image is updated with data (image data) identified by the minimum deformation storage block 18, and stored as new initial image data. The stored image data is transmitted to each of the feature point sampling unit 6, deformation arithmetic block 16, and distortion image operation block 21.

The distortion image operation block 21 is a means for visualizing the displacement (distortion) made by a biological tissue using the images in which the feature point is seen to have been distorted to the variations indicated with the maximum and minimum displacement values.

As mentioned above, the displacement operation unit 7 calculates a distance between a feature point and its counterpart that are associated with each other by the counterpart calculation block 14 on the basis of the coordinates of two pairs of peak points and the associated values thereof (distributions of powers). Thus, the largest and smallest distances are detected.

Moreover, aside from the foregoing hardware configuration, a computer included in the diagnostic ultrasound system may be used to implement a method of time-displaying displacements made by a biological tissue. Namely, displacement values indicating displacements made by a biological tissue of a subject are time-sequentially stored in a storage means, and time-sequentially read from the storage means in order to visualize the displacement values relatively.

When many patients are examined during, for example, mass screening, the diagnostic ultrasound system is used to measure and store a plurality of cross-section images before and after each of the subjects is pressed using the probe. Thereafter, the plurality of stored cross-section images is used to calculate and display displacement values. Measurement of displacement values and diagnosis can be performed independently of each other in a concentrated manner. Consequently, an efficient observation environment can be provided.

Figure 15:
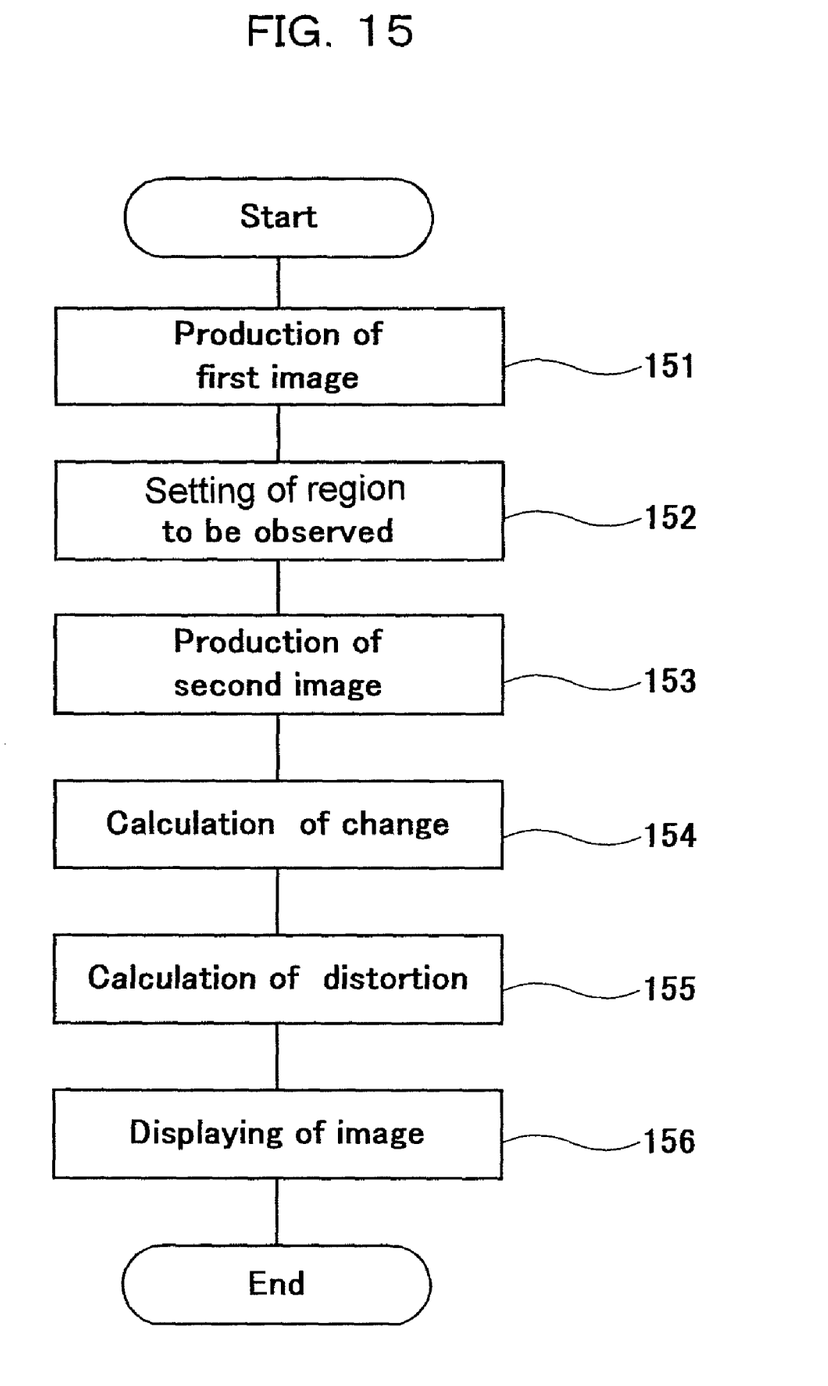
FIG. 15 shows a flowchart describing display of distortion information.

FIG. 15 describes a concrete procedure for implementing a distortion displaying method.

<Producing a first image> Ultrasonic measurement is performed with the probe touched to a subject in a first state in order to produce a first image of the subject (Step 151).

<Delineating a region to be observed> A region to be observed (reference information) is delineated in the produced first image (Step 152). The delineation falls into manual delineation in which a region to be observed is delineated in an image displayed on the display screen, and automatic delineation in which a region in which a distance to a feature point (macro distance) is equal to or larger than a specified value is delineated as a region to be observed. When the automatic delineation technique is adopted, the first image produced by the first image production means is displayed on the image display means, and at least one region-of-interest is delineated in the first image.

When the densities of portions of an image are different from each other, for example, when an image shows a normal tissue and an abnormal tissue, a region supposed to be the abnormal tissue and identified with the density is sampled as a feature point, and the sampled feature point and its surroundings are designated as a region-of-interest.

<Producing a second image> Ultrasonic measurement is performed with the probe touched to the subject in a second state different from the first state in order to produce a second image of the subject (Step 153).

<Calculating a change> A change of the coordinates of an observation point in the second image from the coordinates of a counterpart in the first image is calculated (Step 154).

<Calculating a distortion> A distortion made by a desired region-of-interest is calculated based on the calculated change (Step 155).

<Displaying an image> The calculated distortion information is displayed (Step 156). The Step 153 and subsequent steps may be repeated in order to display a time-sequentially varying second image. The display form has been described previously.

Moreover, the present invention may be implemented in a program for displaying displacements, which are made by a biological tissue, together with an ultrasonic image. In this case, the program is installed in a computer system comprising an input unit that includes a known keyboard, a known mouse, and an interface via which data is received from the diagnostic ultrasound system, a processing unit such as a processor that acts according to a program, and an output unit that includes a monitor on which an image is displayed according to the result of processing. Displacement values indicating displacements made of a biological tissue of a subject are time-sequentially stored in a storage means, and time-sequentially read from the storage means in order to calculate distortion information from the displacement values.

Consequently, when a personal computer owned by an examining physician or a paramedic is adopted as the computer system, the foregoing displaying method can be implemented. Moreover, a program capable of editing the results of diagnosis may be used to produce electronic clinical recordings. Moreover, when the personal computer supports a network environment, secondary utilization of data is enabled, for example, diagnostic information may be provided for individual patients. Wherein, because diagnostic information is personal information that is ranked as a top secret, preferably the information is protected with a perfect security facility.

The invention made by the present inventor has been described in conjunction with the embodiment. The present invention is not limited to the embodiment but may be modified in various manners without a departure from the gist thereof.

The present invention provides an advantage that ultrasonic images are time-sequentially acquired by varying the pressure imposed on the probe, and the softness or hardness of a biological tissue is visualized using a difference between ultrasonic images.

The invention claimed is:

1. A diagnostic ultrasound system comprising:
   a probe configured to measure a subject using ultrasound by bringing said probe into contact with a subject in a first state;
   a first image production means for producing a first image of said subject according to information sent from said probe;
   an image display means for displaying said first image produced by said first image production means;
   a second image production means for producing a second image of said subject according to information measured by bringing the probe into contact with said subject in a second state different from said first state in that pressure is applied to the subject;
   a distortion operation means for calculating distortion information on a desired region-of-interest in said second image corresponding to the desired region-of-interest on said first image;
   a display control means for controlling the display of the distortion information, which is calculated by said distortion operation means, on said image display means;
   a means for setting a reference information and the desired region-of-interest on said first image displayed by said image display means;
   a variation operation means for calculating a macro displacement, which is a positional change of the reference information set on said first image into a counterpart visualized in said second image, and for calculating a micro displacement, which is the deformation change of the region-of-interest in said first image into a counterpart visualized in said second image; and
   a means for displaying the relationship between said macro displacement and said micro displacement calculated by said variation operation means and the distortion information calculated by said distortion operation means.

2. A diagnostic ultrasound system according to claim 1, further comprising a region-of-interest setting means for setting a desired region-of-interest on said first image, wherein the deformation change of the region-of-interest delineated in said first image into a counterpart visualized in said second image is calculated and displayed on said image display means.

3. A diagnostic ultrasound system according to claim 1, wherein said reference information set by said setting means is the two feature points set on said first image at a vicinity point of said probe and at the deepest point from the vicinity of said probe.

4. A diagnostic ultrasound system according to claim 1, wherein said reference information inputted by said setting means is automatically set in a predetermined portion of said first image.

5. A diagnostic ultrasound system according to claim 1, wherein said display control means displays an image of said desired region-of-interest on said image display means in a different display form, that is, in a different color or shape.

6. A diagnostic ultrasound system according to claim 1, further comprising a graph production means for producing a graph indicating the relationship between at least one of statistics including an instantaneous value of a displacement relative to a region in contact with said probe, a cumulative value of displacements, and an average of displacements, and at least one of statistics including a displacement relative to a region-of-interest, wherein
   said display control means displays the graph, which is produced by said graph production means, on said image display means.

7. A diagnostic ultrasound system according to claim 1, further comprising a character string production means for producing a character string, which represents a numerical value of at least one of statistics including an instantaneous value of a displacement relative to region-of-interest in said subject, a cumulative value of displacements, and an average of displacements, wherein said display control means displays the character string, which is produced by said character string production means, on said image display means.

8. A method for displaying information on distortion of biological tissue in ultrasonic image, comprising:
   a first image production step for measuring a subject using ultrasound by bringing a probe into contact with a subject in a first state, and producing a first image of said subject according to the measurement information;
   an image display step for displaying said first image produced at said first image production step;
   a step for setting a reference information and a desired region-of-interest on said first image displayed at said image display step;
   a second image production step for measuring a subject using ultrasound by bringing said probe into contact with said subject in a second state different from said first state in that pressure is applied to the subject, and producing a second image of said subject according to the measurement information;
   a variation operation step for calculating a macro displacement, which is a positional change of the reference information set on said first image into a counterpart visualized in said second image and for calculating a micro displacement, which is the deformation change of the region-of-interest in said first image into a counterpart visualized in said second image;
   a step for seeking a relationship between the macro displacement and the micro displacement calculated at said variation operation; and
   a display control step for controlling the display of said relationship, which is sought at said step for seeking, at said image display step.

9. A method of displaying distortion information on a biological tissue together with an ultrasonic image according to claim 8, wherein: at said variation operation step, a locus of points starting with the point of said reference information set on said first image and ending with the point of a counterpart visualized in said second image is calculated; and at said display control step, the display of said calculated locus at said image display step is controlled.

10. A method of displaying distortion information on a biological tissue together with an ultrasonic image according to claim 8, wherein: at said variation operation step, a change relative to said desired region-of-interest in said second image is calculated; and at said display control step, the display of the calculated change relative to said region-of-interest at said image display step is controlled.

11. A method of displaying distortion information on a biological tissue together with an ultrasonic image according to claim 10, further comprising a step for setting a region-of-interest by delineating a desired region-of-interest in said first image, wherein a change is calculated and displayed; the change is that relative to said region-of-interest delineated in said first image into a counterpart visualized in said second image.

12. A method of displaying distortion information on a biological tissue together with an ultrasonic image according to claim 8, wherein said reference information set at said setting step is visualized in said first image to be located at the deepest point from the vicinity of said probe.

13. A method of displaying distortion information on a biological tissue together with an ultrasonic image according to claim 8, wherein said reference information set at said setting step is automatically delineated in a predetermined portion of said first image.

14. A method of displaying distortion information on a biological tissue together with an ultrasonic image according to claim 8, wherein at said display control step, an image of said desired region-of-interest is displayed in a different display form, that is, in a different color or shape.

15. A diagnostic ultrasound system according to claim 1, wherein said variation operation means further comprises:
a frame-data memorization means for memorizing a plurality of frame-data of reflected echo signals measured by said probe in time series;
an image-data production means for producing an image-data based upon said frame-data read-out from said memorization means; and
a feature point deriving means for deriving said feature points from at least two said image-data corresponding to each other;
wherein said variation operation means calculates the distance between at least said two feature points of said first image and the distance between at least said two feature points of said second image corresponding to said two feature points of said first image, and calculates an amount of change of the distance between said first image and said second image, based upon coordinate data of said feature points of two frame-data corresponding to said first image and said second image, derived by said feature point derive means.

16. A diagnostic ultrasound system according to claim 15, wherein said feature point deriving means further comprises:

a first filtering means for selectively passing a spatial frequency of said frame-data read-out from said frame-data memorization means;
a power calculation means for calculating a distribution of power of the frame-data output from said first filtering means;
a weighting means for applying a weight to a distribution of power output from said power calculation means;
a clustering means for detecting two peak points in the distribution of power applied the weight output from said weighting means and retrieving the value associated with the peak points;
a correlation pre-processing means for processing a distribution of weight by fitting a predetermined weighting function to the peak points and the value output from said clustering means;
a second filtering means for selectively passing a spatial frequency of initial frame-data read-out from said frame-data memorization means;
a cross-correlation means for calculating a distribution of correlations between the distribution of weights output from said correlation pre-processing means and the distribution of power output from said second filtering means; and
a counterpart calculation means for detecting two peak points in the distribution of correlations output from said cross-correlation means and for retrieving the value associated with the peak points;
wherein said variation operation means calculates said amount of change of the distance by calculating a difference of the distance between the two peak points obtained by said correlation pre-processing means and the two peak points obtained by said counterpart calculation means.

17. A diagnostic ultrasound system according to claim 15, wherein said variation operation means further comprises:
a deformation arithmetic means for calculating the distance of two peak points and a positive or negative sign of moving direction;
a maximum deformation image storage means for identifying and storing an image in which the change of the distance of the two peak points and the positive or negative sign of moving direction are seen to have the greatest extent;
a minimum deformation image storage means for identifying and storing an image in which the distance of the two peak points and the positive or negative sign of moving direction are seen to have the smallest extent;
an initial image storage means for storing an image in which the distance of the two peak points and the positive or negative sign of moving direction are finally smallest;
a final image storage means for storing an image in which the distance of the two peak points and the positive or negative sign of moving direction are finally greatest; and
a distortion image operation means for visualizing the distortion of a biological tissue using the images stored in said final image storage means and said final image storage means.

* * * * *